US010494365B2

(12) United States Patent
Cantley et al.

(10) Patent No.: US 10,494,365 B2
(45) Date of Patent: Dec. 3, 2019

(54) SMALL MOLECULE INHIBITOR OF 3-PHOSPHOGLYCERATE DEHYDROGENASE AND USES THEREOF

(71) Applicants: The Scripps Research Institute, La Jolla, CA (US); Cornell University, Ithaca, NY (US)

(72) Inventors: Lewis C. Cantley, Cambridge, MA (US); Edouard Mullarky, New York, NY (US); Costas Lyssiotis, Ann Arbor, MI (US); Luke L. Lairson, San Diego, CA (US); Natasha Lucki, San Diego, CA (US)

(73) Assignees: Cornell University, Ithica, NY (US); The Scripps Research Institute, La Jolla, CA (US)

( * ) Notice: Subject to any disclaimer, the term of this patent is extended or adjusted under 35 U.S.C. 154(b) by 0 days.

(21) Appl. No.: 16/067,141

(22) PCT Filed: Dec. 30, 2016

(86) PCT No.: PCT/US2016/069496
§ 371 (c)(1),
(2) Date: Jun. 29, 2018

(87) PCT Pub. No.: WO2017/117532
PCT Pub. Date: Jul. 6, 2017

(65) Prior Publication Data
US 2019/0010144 A1    Jan. 10, 2019

Related U.S. Application Data

(60) Provisional application No. 62/273,691, filed on Dec. 31, 2015.

(51) Int. Cl.
*C07D 409/12* (2006.01)
*A61P 35/00* (2006.01)

(52) U.S. Cl.
CPC ............ *C07D 409/12* (2013.01); *A61P 35/00* (2018.01)

(58) Field of Classification Search
CPC .................................................. C07D 409/12
USPC ......................................................... 549/63
See application file for complete search history.

(56) References Cited

U.S. PATENT DOCUMENTS

2007/0105864 A1    5/2007    Guzi et al.

FOREIGN PATENT DOCUMENTS

| WO | WO-2005044008 A2 | 5/2005 |
| WO | WO-2006040569 A1 | 4/2006 |
| WO | WO-2017117532 A1 | 7/2017 |

OTHER PUBLICATIONS

"International Application Serial No. PCT/US2016/069496, International Search Report dated Mar. 17, 2017", 4 pgs.
"International Application Serial No. PCT/US2016/069496, Written Opinion dated Mar. 17, 2017", 8 pgs.
Edouard, Mullarky, et al., "Identification of a small molecule inhibitor of 3-phosphoglycerate dehydrogenase to target serine biosynthesis in cancers", Proceedings National Academy of Sciences PNAS, vol. 113, No. 7, (Feb. 16, 2016), 1778-1783.
Recep, Nigdelioglu, et al., "Transforming Growth Factor (TGF)-[beta] Promotes de Novo Serine Synthesis for Collagen Production", Journal of Biological Chemistry, vol. 291, No. 53, (Nov. 11, 2016), 27239-27251.
"International Application Serial No. PCT/US2016/069496, International Preliminary Report on Patentability dated Jul. 12, 2018", 10 pgs.
Ambrogi, Valeria, et al., "Convenient Synthesis of 2-Aminonaphthalene-1-thiol and 3-Aminoquinoline-4-thiol and Cyclocondensations to 1,4-Thiazino and 1,4-Thiazepino Derivatives", Synthesis, 1992(7), (Jul. 1992), 656-658.
Anastasiou, Dimitrios, et al., "Pyruvate kinase M2 activators promote tetramer formation and suppress tumorigenesis", Nature Chemical Biology, 8, (Oct. 2012), 839-847 (total of 10 pgs.).
Antoniewicz, Maciek R., "Determination of confidence intervals of metabolic fluxes estimated from stable isotope measurements", Metabolic Engineering, 8, (2006), 324-337.
Antoniewicz, Maciek R., et al., "Elementary metabolite units (EMU): A novel framework for modeling isotopic distributions", Metabolic Engineering, 9(1), (2007), 68-86.
Barker, G. A., et al., "The ldentfication of Neutral Amino Acid Transport Systems", Experimental Physiology, 75(1), (1990), 3-26.
Barretina, Jordi, et al., "The Cancer Cell Line Encyclopedia enables predictive modelling of anticancer drug sensitivity", Nature, 483(7391), (2012), 603-607 (total of 6 pgs.).
Beroukhim, Rameen, et al., "The landscape of somatic copy-number alteration across human cancers", Nature, 463, (2010), 899-905.
Boolell, Vishal, et al., "The Evolution of Therapies in Non-Small Cell Lung Cancer", Cancers, 7, (2015), 1815-1846.
Buescher, Joerg M., et al., "A roadmap for interpreting $^{13}$C metabolite labeling patterns from cells", Current Opinion in Biotechnology, 34, (2015), 189-201.
Dang, Lenny, et al., "Cancer-associated IDH1 mutations produce 2-hydroxyglutarate", Nature, 465, (2010), p. 966.
De Koning, Tom J., et al., "L-Serine in disease and development", Biochem. J., 372, (2003), 653-661.
Denicola, Gina M., et al., "NRF2 regulates serine biosynthesis in non-small cell lung cancer", Nature Genetics, 47(12), (2015), 1475-1481 (total of 10 pgs.).
Foulkes, William D., et al., "Triple-Negative Breast Cancer", N Engl J Med., 363(20), (2010), 1938-1948.
Futerman, Anthony H., et al., "The ins and outs of sphingolipid synthesis", Trends Cell Biol 15(6), (2005), 312-318.

(Continued)

*Primary Examiner* — Taofiq A Solola
(74) *Attorney, Agent, or Firm* — Schwegman Lundberg & Woessner, P.A.

(57) ABSTRACT

Embodiments of the present invention are directed to small molecule inhibitors of PHGDH. Other embodiments of the present invention relate to methods of treating cancers using the small molecule inhibitors of PHGDH disclosed herein. Still other embodiments of the present invention relate to methods for using the small molecule inhibitors of PHGDH to study serine metabolism.

21 Claims, 6 Drawing Sheets

(56) References Cited

OTHER PUBLICATIONS

Gottlieb, Eyal, et al., "Mitochondrial Tumour Suppressors: A Genetic and Biochemical Update", Nature Review Cancer, 5, (Nov. 2005), 857-866.
Hitosugi, Taro, et al., "Phosphoglycerate Mutase 1 Coordinates Glycolysis and Biosynthesis to Promote Tumor Growth", Cancer Cell, 22, (2012), 585-600.
Kuge, Osamu, et al., "Control of Phosphatidylserine Biosynthesis through Phosphatidylserine-Mediated Inhibition of Phosphatidylserine Synthase I in Chinese Hamster Ovary Cells", Proc. Natl. Acad. Sci. USA, 95(8), (1998), 4199-4203.
Kung, Charles, et al., "Small Molecule Activation of PKM2 in Cancer Cells Induces Serine Auxotrophy", Chemistry & Biology, 19, (2012), 1187-1198.
Locasale, Jason W., et al., "Phosphoglycerate dehydrogenase diverts glycolytic flux and contributes to oncogenesis", Nature Genetics, 43(9), (2011), 869-874 (total of 8 pgs.).
Mullarky, Edouard, et al., "PHGDH amplification and altered glucose metabolism in human melanoma", Pigment Cell Melanoma Res., 24, (2011), 1112-1115.
Mullen, Andrew R., et al., "Genetically-defined metabolic reprogramming in cancer", Trends in Endocrinology and Metabolism, 23(11), (Nov. 2012), 552-559.
Nicolay, Brandon N., et al., "Loss of RBF1 changes glutamine catabolism", Genes & Development, 27, (2013), 182-196.
Palacín, Manuel, et al., "Molecular Biology of Mammalian Plasma Membrane Amino Acid Transporters", Physiological Reviews, 78(4), (Oct. 1998), 969-1054.
Parsons, D. Williams, et al., "An Integrated Genomic Analysis of Human Glioblastoma Multiforme", Science, 321, (2008), 1807-1812.
Pollari, Sirkku, et al., "Enhanced serine production by bone metastatic breast cancer cells stimulates osteoclastogenesis", Breast Cancer Res Treat., 125, (421-430), 2011.
Possemato, Richard, et al., "Functional genomics reveal that the serine synthesis pathway is essential in breast cancer", Nature, 476, (2011), 346-350 (total of 8 pgs.).
Rohle, Dan, et al., "An Inhibitor of Mutant IDH1 Delays Growth and Promotes Differentiation of Glioma Cells", Science, 340 (6132), (2013), 626-630.
Snell, K., et al., "Enzymic imbalance in serine metabolism in human colon carcinoma and rat sarcoma", Br. J. Cancer,57(1), (1988), 87-90.
Snell, Keith, et al., "The duality of pathways for serine biosynthesis is a fallacy", TIBS,11, (Jun. 1986), 241-243.
Snell, Keith, et al., "The modulation of serine metabolism in hepatoma 3924A during different phases of cellular proliferation in culture", Biochem. J., 245, (1987), 609-612.
Son, Jaekyoung, et al., "Glutamine supports pancreatic cancer growth through a KRAS-regulated metabolic pathway", Nature, 496, (2013), 101-105 (total of 7 pgs.).
Stover, Patrick, et al., "Serine Hydroxymethyltransferase Catalyzes the Hydrolysis of 5,10-Methenyltetrahydrofolate to 5-Formyltetrahydrofolate", The Journal of Biological Chemistry, 265(24), (1990), 14227-14233.
Tennant, Daniel A., et al., "Targeting metabolic transformation for cancer therapy", Nature Reviews Cancer, 10, (Apr. 2010), 267-277.
Tibbetts, Anne S., et al., "Compartmentalization of Mammalian Folate-Mediated One-Carbon Metabolism", Annu. Rev. Nutr., 30(1), (2010), 57-81 (total of 31 pgs., including C-1-C-4).
Vallari, Robert C., et al., "Human Aldehyde Dehydrogenase: Mechanism of Inhibition by Disulfiram", Science, 216(4546), (1982), 637-639.
Wang, Fang, et al., "Targeted Inhibition of Mutant IDH2 in Leukemia Cells Induces Cellular Differentiation", Science, 340(6132), (2013), 622-626.
Ying, Haoqiang, et al., "Oncogenic Kras Maintains Pancreatic Tumors through Regulation of Anabolic Glucose Metabolism", Cell, 149, (2012), 656-670.
Yuan, Min, et al., "A positive/negative ion-switching, targeted mass spectrometry-based metabolomics platform for bodily fluids, cells, and fresh and fixed tissue", Nature Protocols,7(5), (2012), 872-881.
Zhang, Ji-Hu, et al., "A Simple Statistical Parameter for Use in Evaluation and Validation of High Throughput Screening Assays", J. Biomol. Screen, 4(2), (1999), 67-73.

SMALL MOLECULE INHIBITOR OF 3-PHOSPHOGLYCERATE DEHYDROGENASE AND USES THEREOF

CROSS-REFERENCE TO RELATED APPLICATIONS

This application is a U.S. National Stage Filing under 35 U.S.C. 371 from international Application No. PCT/US2016/069496 filed Dec. 30, 2016 and published as WO 2017/117532 on Jul. 6, 2017, which claims benefit of priority to the filing date of U.S. Provisional Application Ser. No. 62/273,691, filed Dec. 31, 2015, the contents of which are specifically incorporated by reference herein in their entity.

STATEMENT OF GOVERNMENT SUPPORT

This invention was made with government support under grant 5P01 CA 120964-09 awarded by the National Institutes of Health. The government has certain rights in the invention.

BACKGROUND

Serine is required for a plethora of anabolic processes. Serine is an abundant component of proteins and is required for the synthesis of lipids including sphingolipids and phosphatidylserine, a major component of cellular membranes. Alternatively, serine hydroxymethyltransferases (SHMTs) convert serine to glycine concomitantly charging the folate pool with "one-carbon" units. Both glycine and folate one-carbon units are used to make nucleotides. Thus, serine serves numerous critically important roles in cellular metabolism.

At the cellular level, serine can be imported from the extracellular space via amino acid transporters. Alternatively, serine can be synthesized from glucose via the phosphoserine pathway. De novo synthesis proceeds from the glycolytic intermediate 3-phosphoglycerate (3-PG) via three sequential enzymatic reactions, the first of which is catalyzed by the NAD+ dependent enzyme 3-phosphoglycerate dehydrogenase (PHGDH). For decades, it has been known that cancer cells have enhanced serine synthesis, which contributes to nucleotide synthesis. Recently, focal amplifications of the gene encoding PHGDH have been reported, particularly in breast cancers and melanomas. Additionally, KEAP1 and NRF2 mutant non-small cell lung cancers (NSCLC) overexpress PHGDH. Proliferation of PHGDH amplified cancer cell lines, and other lines that overexpress PHGDH without amplification, is inhibited by PHGDH knockdown. In contrast, lines that express little PHGDH are resistant to shRNA mediated ablation of the pathway presumably because serine import suffices. A detailed mechanistic understanding of why some cancer cells are "acidicted" to serine synthesis despite the availability of extracellular serine for import remains unclear. Interestingly, in triple negative breast cancer (TNBC) and NSCLC, PHGDH amplification and overexpression are associated with more aggressive disease.

SUMMARY

PHGDH inhibitors as a targeted therapy for the aforementioned tumor types represents an exciting clinical opportunity. To that end, embodiments of the present invention are directed to small molecule inhibitors (e.g., compounds of the formula (I), described herein) of PHGDH. Other embodiments of the present invention relate to methods of treating cancer(s) using the small molecule inhibitors of PHGDH disclosed herein. Still other embodiments of the present invention relate to methods for using the small molecule inhibitors of PHGDH to study serine metabolism. Yet other embodiments, relate to small molecule compounds that decrease de novo serine synthesis, in some instances by at least about 20%, at least about 30%, at least about 40%, at least about 50% or at least about 60%; at most about 30%, at most about 40%, at most about 50%, at most about 60% at most about 70%, at most about 80%, at most about 90% or at most about 100%; or from about 20% to about 50%, about 25% to about 45%, about 30% to about 60% or about 35% to about 55%. In some instances, the de novo serine synthesis can be decreased by disrupting the biosynthesis of 3-phophoglycerate (3-PG), which, in turn, disrupts the biosynthesis of pyruvate and lactate.

DESCRIPTION OF THE DRAWINGS

The drawings illustrate generally, by way of example, but not by way of limitation, various embodiments discussed herein.

DESCRIPTION

Figure 1:
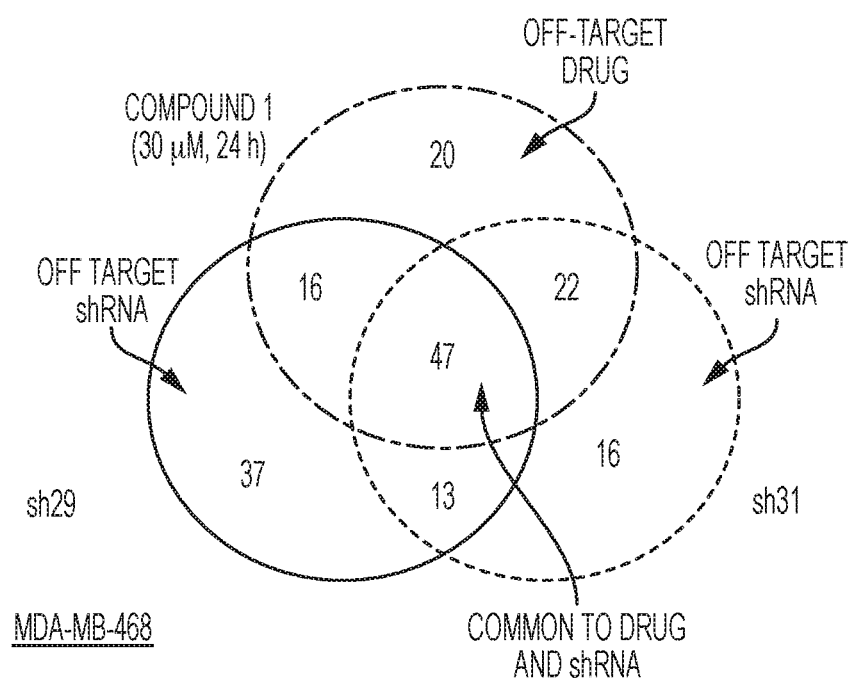
FIG. 1 is a Venn diagram depicting the results to indicate the number of changed metabolites that are changed uniquely or in common across different experimental conditions.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Various embodiments of the present invention are directed to a compound of the formula (I):

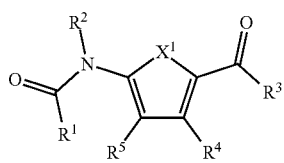

or a pharmaceutically acceptable salt, polymorph, prodrug, solvate or clathrate thereof, wherein: $R^1$ is substituted or unsubstituted aryl, substituted or unsubstituted arylalkyl or substituted or unsubstituted heteroaryl; $R^2$ is hydrogen or substituted or unsubstituted alkyl; $X^1$ is O or S; $R^3$ is —$NR^6R^7$ or —$OR^6$, wherein $R^6$ and $R^7$ are each, independently, hydrogen or substituted or unsubstituted alkyl; $R^4$ is substituted or unsubstituted aryl or substituted or unsubstituted alkyl; and $R^5$ is hydrogen, halo, —C≡N or —$SR^8$, wherein $R^8$ is hydrogen, substituted or unsubstituted alkyl, substituted or unsubstituted aryl or —C≡N.

Various other embodiments of the present invention are directed to a compound of the formula (I):

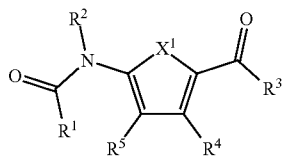

or a pharmaceutically acceptable salt, polymorph, prodrug, solvate or clathrate thereof, wherein: $R^1$ is substituted or unsubstituted aryl, substituted or unsubstituted arylalkyl or substituted or unsubstituted heteroaryl; $R^2$ is hydrogen or substituted or unsubstituted alkyl; $X^1$ is O or S; $R^3$ is —$NR^8R^7$ or —$OR^6$, wherein $R^6$ and $R^7$ are each, independently, hydrogen or substituted or unsubstituted alkyl; $R^4$ is substituted or unsubstituted aryl or substituted or unsubstituted alkyl; and $R^5$ is halo or —$SR^8$, wherein $R^8$ is hydrogen, substituted or unsubstituted alkyl, substituted or unsubstituted aryl or —C≡N.

In some embodiments, $X^1$, in compounds of the formula (I), is S. In some embodiments, in compounds of the formula (I), $R^1$ is substituted or unsubstituted heteroaryl (e.g., furanyl). In some embodiments, in compounds of the formula (I), $R^1$ is substituted or unsubstituted aryl. In still other embodiments, in compounds of the formula (I), $R^2$ is hydrogen. In yet other embodiments, in compounds of the formula (I), $R^3$ is —$OR^6$ (e.g., —$OR^6$ forms an alkoxy group, such as an ethoxy group) and $R^4$ is substituted or unsubstituted alkyl. In yet other embodiments, in compounds of the formula (I), $R^6$ is substituted or unsubstituted alkyl. In other embodiments, in the compounds of the formula (I), $R^5$ is —$SR^8$. In some embodiments, $R^8$ is —C≡N.

Examples of compounds of the formula (I) include compounds selected from the group consisting of:

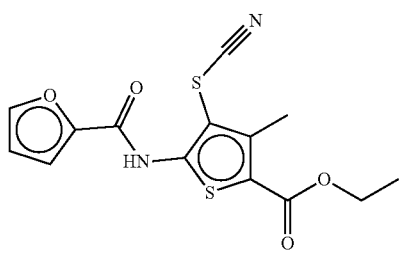

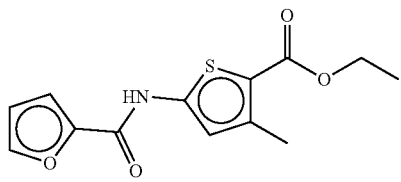

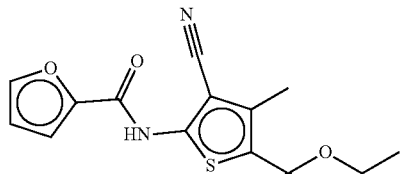

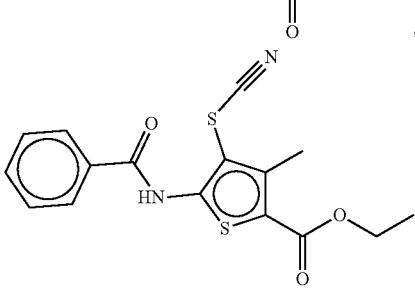

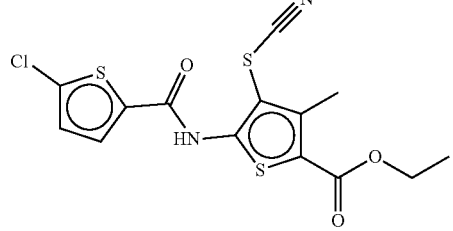

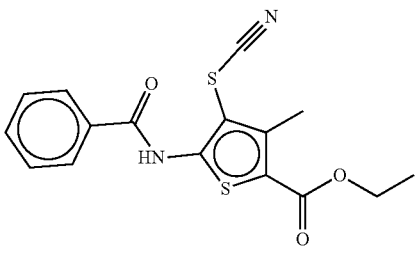

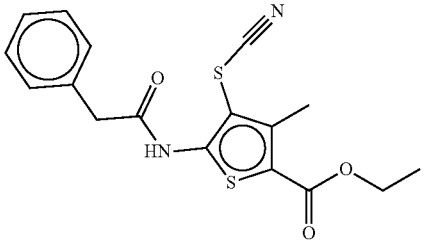

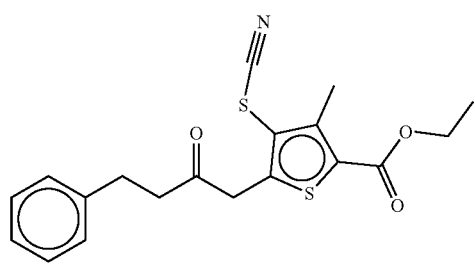

Those of ordinary skill in the art will recognize that compounds described herein can contain chiral centers. All diastereomers of the compounds described herein are contemplated herein, as well as racemates.

Various embodiments of the present invention also contemplate pharmaceutical compositions comprising one or more compounds of the various embodiments of the present invention and one or more pharmaceutically acceptable carriers, diluents, excipients or combinations thereof. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardiac intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions of the present invention may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions of the present invention may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments of the present invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form." as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds of the present invention or an appropriate pharmaceutical composition thereof are effective, the compounds of the present invention may be administered in an effective amount. The dosages as suitable for this invention may be a composition, a pharmaceutical composition or any other compositions described herein.

For each of the recited embodiments, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one embodiment, the dosage may be administered daily for up to and including 30 days, preferably between 7-10 days. In another embodiment, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

In some embodiments, the various embodiments of the present invention contemplate compositions comprising a therapeutically effective amount of one or more compounds of the various embodiments of the present invention. In some embodiments, the compositions are useful in a method for treating cancer, the method comprising administering a therapeutically effective amount of one or more compounds to a patient in need thereof. In some aspects, the various embodiments of the present invention contemplate a compound of the formula (I) for use as a medicament for treating a patient in need of relief from cancer.

The term "therapeutically effective amount" as used herein, refers to that amount of one or more compounds of the various embodiments of the present invention that elicits a biological or medicinal response in a tissue system, animal or human, that is being sought by a researcher, veterinarian, medical doctor or other clinician, which includes alleviation of the symptoms of the disease or disorder being treated. In some embodiments, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds desorbed herein.

In some embodiments, the compounds of the various embodiments of the present invention have a half maximal inhibitory concentration ($IC_{50}$) of from about 500 nM to about 900 µM (e.g., about 500 nM to about 600 µM, about 1 µM to about 600 µM, about 10 µM to about 100 µM, about 10 µM to about 100 µM, about 50 µM to about 300 µM, about 100 µM to about 500 µM or about 10 µM to about 100 µM).

Some embodiments are directed to a method of inhibiting 3-phosphoglycerate dehydrogenase (PHGDH) in a cellular environment comprising contacting the cellular environment with an effective amount of a compound of the formula (I):

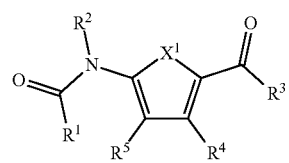

or a pharmaceutically acceptable salt, polymorph, prodrug, solvate or clathrate thereof, wherein: $R^1$ is substituted or unsubstituted aryl, substituted or unsubstituted arylalkyl or substituted or unsubstituted heteroaryl; $R^2$ is hydrogen or substituted or unsubstituted alkyl; $X^1$ is O or S; $R^3$ is —NR$^6$R$^7$ or —OR$^6$, wherein R$^6$ and R$^7$ are each, independently, hydrogen or substituted or unsubstituted alkyl; R$^4$ is substituted or unsubstituted aryl or substituted or unsubstituted alkyl; and R$^5$ is hydrogen, halo, —C≡N or —SR$^8$, wherein R$^8$ is hydrogen, substituted or unsubstituted alkyl, substituted or unsubstituted aryl or —C≡N. In some embodiments, X$^1$ is S. In other embodiments, R$^1$ is substituted or unsubstituted heteroaryl or substituted or unsubstituted aryl. In still other embodiments, R$^5$ is —SR$^8$. In yet other embodiments, R$^8$ is —C≡N. The "cellular environment" can be in vivo or in vitro.

Compounds of the formula (I) are suitable for use as a medicament for treating a patient in need of relief from cancer. In some embodiments, compounds of the formula (I) are at least 4-fold, at least 10-fold, or at least 100-fold more selective for PHGDH than other NAD(P)$^+$ dependent dehydrogenases. In some embodiments, the other NAD(P)$^+$ dependent dehydrogenases are selected from the group consisting of lactate dehydrogenase (LDH), 3α-hydroxysteroid dehydrogenase (3α-HSD), diaphorase, isocitrate dehydrogenase (IDH1), and malate dehydrogenase (MDH1).

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substituted" as used herein refers to a group (e.g., alkyl, aryl, and heteroaryl) or molecule in which one or more hydrogen atoms contained thereon are replaced by one or more substituents. The term "substituent" as used herein refers to a group that can be or is substituted onto a molecule or onto a group. Examples of substituents include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be, for example, hydrogen, alkyl, acyl, cycloalkyl, aryl, aralkyl, heterocyclyl, heteroaryl, or heteroarylalkyl.

The term "alkyl" as used herein refers to substituted or unsubstituted straight chain and branched alkyl groups and cycloalkyl groups having from 1 to 40 carbon atoms (C$_1$-C$_{40}$), 1 to about 20 carbon atoms (C$_1$-C$_{20}$), 1 to 12 carbons (C$_1$-C$_{12}$), 1 to 8 carbon atoms (C$_1$-C$_8$), or, in some embodiments, from 1 to 6 carbon atoms (C$_1$-C$_6$) or 1 to 3 (C$_1$-C$_3$) carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed herein, for example, amino, hydroxy, cyano, carboxy, nitro, thio, alkoxy, and halogen groups.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms (C$_3$-C$_6$). Cycloalkyl groups further include polycyclic cycloalkyl groups such as, but not limited to, norbornyl, adamantyl, bornyl, camphanyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be monosubstituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups.

The term "heterocyclyl" as used herein refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazyolyl, tetrazolyl, benzoxazolinyl, and benzimidazolinyl groups.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, oxopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to alkylamines, arylamines, arylalkylamines; dialkylamines, diarylamines, dialkylamines, heterocyclylamines and the like; and ammonium ions.

The terms "halo." "halogen," or "halide" group, as used herein, by themselves or as part of another substituent, mean, unless otherwise stated, a fluorine, chlorine, bromine, or iodine atom.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic add salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic adds. For example, such conventional non-toxic salts include those derived from inorganic acids such as hydrochloric, hydrobromic, sulfuric, sulfamic, phosphoric, and nitric; and the salts prepared from organic adds such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or add in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

EXAMPLES

The present invention can be better understood by reference to the following examples which are offered by way of illustration. The present invention is not limited to the examples given herein.
Materials and Methods
Cells, Transfections, and Infections:
Breast and melanoma lines were passaged in RPMI supplemented with: 10% FBS, penicillin, streptomycin, and normocin (InvivoGen). Lentivirus was produced from Lenti-X 293T cells (Clontech) transfected with packaging plasmids pCMV-dR8.2 and pCMV-VSV-G and indicated pLKO.1 shRNAs: PHGDH, TRCN0000233029 (sh1) and TRCN0000221864 (sh2); nontargeting control. TRCN0000072181 (shGFP).
Immunoblots:
Protein was extracted from cells via trichloroacetic acid precipitation and blotted for with primary antibodies: αPHGDH (Sigma HPA021241, 1/10000); αVinculin (Sigma V9264, 1/5000).
Proliferation Assays:
Cells were plated at a low density in 96 or 24 well plates in serine containing media. The following day, media was aspirated, cells were washed with PBS, and fresh serine replete or deplete media containing drug (15 µM, 30 µM) or vehicle (DMSO) was added. Cells were grown for 3 to 5 days, with drug and media changed daily before assaying relative cell numbers.
Acute Drug Treatments with $^{13}C_6$-Glucose Tracing:
Carney cells acclimated to growth in MEM (Corning) were plated at $9 \times 10^5$ cells per 6 cm dish the night before. The following morning, media was replaced with fresh media containing (1) (1 µM, 15 µM, 30 µM) or vehicle control (DMSO) for 1h. Media was then aspirated, cells were washed with PBS, and fresh glucose free MEM (Gibco) supplemented with $^{13}C_6$-glucose (3 g/L, Cambridge Isotopes) and 10% dialyzed FBS containing drug or DMSO was added. After 2h, cells were quickly washed with cold PBS on ice and flash frozen. Polar metabolites were extracted as in the GCMS methods.
Acute Toxicity Assay:
Carney cells acclimated to growth in MEM media were plated in a 96 well plate at 6,000 cells/well. The next day, cells were treated with (1) from 1 µM to 40 µM for 3h. Drug containing media was then removed, fresh drug-free media added, and cell viability was determined via a CellTiter-Glo (Promega G7572) or Alamar Blue (Invitrogen DAL1025) assay according to the manufacturer's protocol.
GCMS Metabolite Analysis:
Polar metabolites were extracted with 2 ml MeOH/H$_2$O (4:1) for 30 min on dry ice, scraped, transferred to 2 ml tubes, centrifuged (30 min, 15000 rpm), and the supernatants dried under vacuum. Samples were derivatized as previously described and analyzed on an Agilent 6890 GC instrument. Metabolite quantification was inferred from a standard curve and fractional enrichment of $^{13}C$ in metabolites was corrected for the natural abundance of $^{13}C$ and $^{15}N$.

LC-MS/MS Metabolite Analysis:
Polar metabolites were extracted and dried as in the GCMS method. Samples were resuspended in 15 µl of HPLC grade water. 5 µl of each sample was injected and analyzed using a 5500 QTRAP triple quadrupole mass spectrometer (AB/Sciex) coupled to a Prominence UFLC system (Shimadzu) as reported previously.
Protein Purification:
His$_6$-tagged pET28a PHGDH, pET28a PSAT1, and pNIC28-Bsa4 PHGDH$^{3-314}$ were purified via nickel agarose (Qiagen) from BL21 *E. coli* cultures, pVB-CBD IDH1 was purified via Macroporous Bead Cellulose capture, TEV protease (Sigma-Aldrich) digestion, and gel filtration chromatography from BL21 *E. coli* cultures.
PHGDH Assays:
PHGDH activity was measured in 96-well plates by monitoring NADH fluorescence (Ex340 nM/Em460 nM) over time. PSAT1 was included to prevent product inhibition of PHGDH.
LDH and MDH1 Assays:
Enzyme activities were assayed using kits (LDH: Sigma MAK06; MDH1: Sigma MAK196-1KT) according to the manufacturer's instructions with commercially available recombinant enzyme (LDH: Sigma 59747; MDH1: Sigma SRP6103). Drug, titrated as for the PHGDH IC$_{50}$ assays, and enzyme were pre-incubated for 30 min prior to initiating reaction with substrate
Cross-Linking Assays:
PHGDH (1.5 µg) or LDH (2.2 µg, Sigma 59747) were incubated with (1) (50 µM, 200 µM, 400 µM) or vehicle control (DMSO) in 25 mM HEPES, pH 7.3, and 1 mM NAD$^+$ in 18 µL total volume for 30 min prior to BS3 (Pierce) cross-linking and quenching. Samples were run on SDS-PAGE and colloidal coomassie stained (Bio-Rad).
Primary PHGDH Screen, Diaphorase Counter Screen, and Dehydrogenase Panel Selectivity Profiling:
800,000 compounds were screened at a single dose (13.3 µM) in 1536-plate format against PHGDH or diaphorase quantifying resorufin fluorescence (550/590 nm; Ex/Em) with an Envision plate reader. Results were analyzed using Genedata Screener software. Compounds with a robust Z-score<−3 in the PHGDH screening assay and robust Z-score>−2 in the diaphorase counter screen were selected as hits.

Example 1: Synthesis

The compounds of the various embodiments can be synthesized as described in the following examples.
Materials:
2-amino-4-methyl-3-cyanato-5-thiophenecarboxylate ethyl ester, was obtained from Life Chemicals. Cyanoacetic acid was obtained from AK Scientific. All remaining reagents and solvents were obtained from Sigma-Aldrich. All reagents were used as received without further purification.

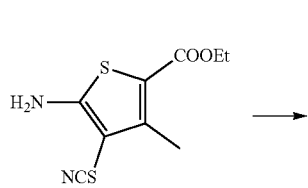

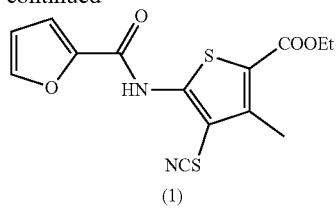

Ethyl 5-(furan-2-carboxamido)-3-methyl-4-thiocyanatothiophene-2-carboxylate (1)

86.3 mg 2-amino-4-methyl-3-cyanato-5-thiophenecarboxylate ethyl ester (357 μmol, 1 eq.) was suspended in 1 mL DCM with a magnetic stirbar. 86.5 μL of pyridine (1070 μmol, 3 eq.) was added to the mixture, followed by dropwise addition of 35.3 μL 2-furoyl chloride (357 μmol, 1 eq.). After 1 hour the reaction mixture was purified directly by normal-phase silica gel chromatography. Collected fractions were dried in vacuo to obtain 87.2 mg ethyl 5-(furan-2-carboxamido)-3-methyl-4-thiocyanatothiophene-2-carboxylate as a white solid, 73% yield. $^1$H NMR (400 MHz CDCl$_3$) δ 9.36 (s, 1H), 7.67 (dd, J=0.8, 1.7 Hz, 1H), 7.41 (dd, J=0.8, 3.6 Hz, 1H), 6.67 (dd, J=1.7, 3.6 Hz, 1H), 4.36 (q, J=7.1 Hz, 2H), 1.40 (t, J=7.1 Hz, 3H) ppm. LC-MS (M+H)$^+$=337.09, (M-CN)$^+$=310.09.

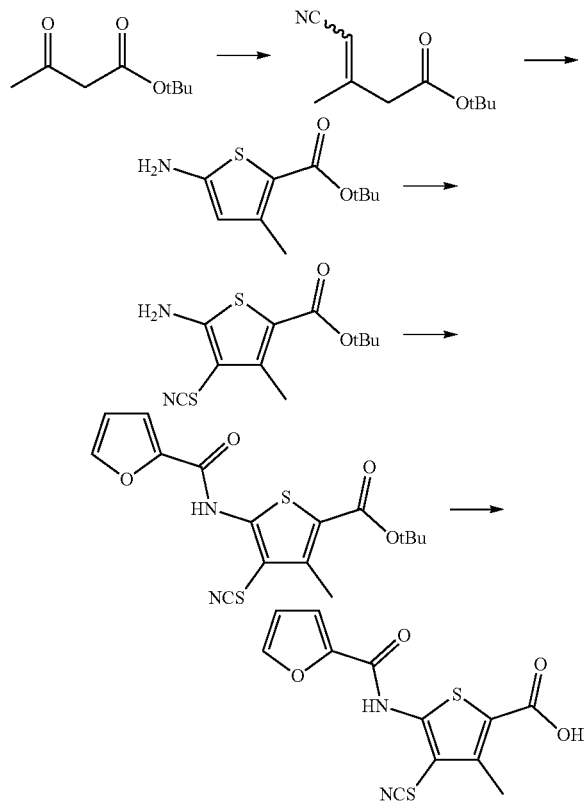

Tert-butyl 4-cyano-3-methylbut-3-enoate 5.00 g (36.1 mmol, 1 eq.) tert-butyl acetoacetate, 2.69 g (31.6 1 eq.) cyanoacetic acid, and 488 mg (6.33 mmol, 0.2 eq.) ammonium acetate were added to a solution of 0.9 mL acetic acid and 9.0 mL benzene. The reaction mixture was refluxed in a Dean-Stark trap for 24 hours. After cooling to room temperature, the reaction mixture was washed with saturated sodium bicarbonate, brine, then dried with sodium sulfate and condensed in vacuo. The crude product was vacuum-distilled at 65° C. to obtain 1.28 g tert-butyl 4-cyano-3-methylbut-3-enoate as a mixture of E/Z isomers, 23% yield, clear oil. $^1$H NMR (400 MHz CDCl$_3$) δ 5.30 (m, 2H), 3.36 (d, J=1.5 Hz, 1H), 3.11 (d, J=1.1 Hz, 1H), 2.15 (d, J=1.1 Hz, 1H), 2.02 (d, J=1.5 Hz, 1H), 1.48 (m, 18H) ppm.

Tert-butyl 5-amino-3-methylthiophene-2-carboxylate 1.28 g (7.09 mmol, 1 eq.) tert-butyl 4-cyano-3-methylbut-3-enoate and 227 mg (7.09 mmol, 1 eq.) sulfur flakes were suspended in 5.5 mL ethanol. 806 μL (7.80 mmol, 1.1 eq.) diethylamine was added drop-wise and the mixture was stirred for 4 hours, forming a dark orange/red solution. Reaction mixture was dried in vacuo and purified by flash chromatography. After drying collected fractions in vacuo, 814 mg tert-butyl 5-amino-3-methylthiophene-2-carboxylate was obtained as a yellow-orange oil, 54% yield. $^1$H NMR (400 MHz CDCl$_3$) δ 5.99 (s, 1H), 4.01 (br, s, 2H), 2.40 (s, 3H), 1.552 (s, 9H) ppm.

Tert-butyl 5-amino-3-methyl-4-thiocyanatothiophene-2-carboxylate 100 mg (0.469 mmol, 1 eq.) tertbutyl 5-amino-3-methylthiophene-2-carboxylate and 71.4 mg (0.938 mmol, 2 eq.) ammonium thiocyanate were dissolved in 0.5 mL methanol and cooled with an ice bath. A solution of 14.9 μL (0.291, 0.62 eq.) bromine in methanol was added drop-wise to the reaction mixture. The mixture was stirred on ice for 10 minutes; then the ice bath was removed and the mixture stirred for another hour while warming to room temperature. The reaction mixture was then dried in vacuo and purified by flash chromatography. The collected fractions were dried in vacuo to afford 32.0 mg tertbutyl 5-amino-3-methyl-4-thiocyanatothiophene-2-carboxylate as a white solid. $^1$H NMR (400 MHz CDCl$_3$) δ 5.05 (br. s, 1H), 2.59 (2, 3H), 1.57 (s, 9H) ppm.

Tert-butyl 5-(furan-2-carboxamido)-3-methyl-4-thiocyanatothiophene-2-carboxylate Prepared analogously as ethyl 5-(furan-2-carboxamido)-3-methyl-4-thiocyanatothiophene-2-carboxylate. From 32.0 mg (0.119 mmol) tertbutyl 5-amino-3-methyl-4-thiocyanatothiophene-2-carboxylate as starting material, 19.8 mg tert-butyl 5-(furan-2-carboxamido)-3-methyl-4-thiocyanatothiophene-2-carboxylate was obtained as a white solid, 46% yield.

$^1$H NMR (400 MHz CDCl$_3$) δ 9.35 (s 1H), 7.68 (dd, J=0.8, 1.7 Hz, 1H), 7.42 (dd, J=0.8, 3.6 Hz, 1H), 6.68 (dd, J=1.8, 3.6 Hz, 1H), 2.72 (s, 3H), 1.60 (s, 9H) ppm.

5-(furan-2-carboxamido)-3-methyl-4-thiocyanatothiophene-2-carboxylic Acid 0.25 mL trifluoroacetic acid was added slowly to a solution of 5.3 mg (13.7 μmol) tertbutyl 5-(furan-2-carboxamido)-3-methyl-4-thiocyanatothiophene-2-carboxylate in 0.25 mL dichloromethane in an ice bath and stirred for 30 minutes, allowing the mixture to warm to room temperature over time. The reaction mixture was dried in vacuo with minimal heating applied (no greater than 30° C.). The dried product was sonicated in diethyl ether to dissolve remaining starting material, centrifuged briefly to precipitate the product, then decanted to remove starting material in the ether layer. This ether treatment was repeated two more times. After drying the remaining solid in vacuo, 1.6 mg 5-(furan-2-carboxamido)-3-methyl-4-thiocyanatothiophene-2-carboxylic acid was obtained as a white solid, 38% yield. $^1$H NMR (400 MHz CDCl$_3$) δ 7.89 (dd, J=0.8, 1.8 Hz, 1H), 7.46 (dd, J=0.8, 3.6 Hz, 1H), 6.75 (dd, J=1.8, 3.6 Hz, 1H), 2.71 (s, 3H) ppm. LC-MS (M+H)$^+$=309.0, (M-OH)$^+$=291.0, (M-CN)$^+$=282.0.

Example 2: Compound Screening

Screening for Small Molecule Inhibitors of PHQDH.

An in vitro enzymatic assay for PHGDH activity amenable to high-throughput screening (HTS) was developed by coupling the production of NADH, upon 3PG oxidation, to the reduction of resazurin to resorufin using diaphorase as the coupling enzyme. Thus, resorufin fluorescence served as a proxy for PHGDH activity. The assay was miniaturized to 1536 well format with a Z-factor of >0.75 indicating a high quality assay. A library of 800,000 small molecules was screened in single point format at 13 μM. Setting a threshold Z score of −3, corresponding to at least 50% PHGDH inhibition, gave a 0.5% hit rate yielding 3,906 hits. Putative hits were re-assayed in triplicate and counter screened against diaphorase to rule out false positives targeting diaphorase. The counter screen eliminated 3,498 compounds giving 408 PHGDH inhibitors.

A triaging strategy based on hit potency and selectivity was designed. While not being bound to any specific theory, it was reasoned that inhibitors specific to PHGDH would minimize general cellular toxicity compared to compounds that hit a variety of dehydrogenases. Thus, half maximal inhibitory concentrations (IC$_{50}$) were determined for a panel of NAD(P)$^+$ dependent dehydrogenases that included PHGDH, isocitrate dehydrogenase (IDH1), malate dehydrogenase (MDH1), and 3α-hydroxysteroid dehydrogenase (3α-HSD). Compounds at least 4-fold more selective for PHGDH were progressed for further analysis. Based on this triaging, seven of the most potent PHGDH inhibitors were selected as lead compounds for evaluation in cell-based assays; selected structures are shown.

(1) Inhibits Serine Synthesis in Cells.

Gas chromatography mass-spectrometry (GCMS) with uniformly carbon-13 labeled glucose ($^{13}C_6$-glucose) tracing was used to determine if compounds inhibited serine synthesis in cancer cells. Given the isotopic enrichment of serine, it is possible to decouple newly synthesized serine from extracellular serine or serine that was synthesized prior to tracer addition. Newly synthesized serine has a mass-shift of 3 (M+3) due to the incorporation of glucose-derived $^{13}C$ via 3-PG. The kinetics of serine labeling were investigated. Serine labeling plateaued around 6 hours with ~65% of the serine pool being $^{13}C$ labeled. While not being bound to any particular theory, the plateau phase likely reflects exchange between intra- and extra-cellular serine pools.

With an understanding of serine labeling kinetics, a $^{13}C_6$-glucose tracing assay was designed to acutely interrogate the effects of compounds on serine synthesis. Assaying serine synthesis with a 3-hour compound treatment was preferred to longer treatments to guard against false positives that decrease serine labeling by an indirect effect such as generally compromising cellular viability. (1) was able to decrease de novo serine synthesis by 30%; the remaining compounds had little effect. The dose at which (1) had an effect on serine labeling was consistent with the in vitro biochemical IC$_{50}$ of 33±12 μM for PHGDH. At such concentrations, (1) had no effect on two other NAD$^+$ dependent dehydrogenases, lactate dehydrogenase (LDH) and MDH1. Importantly, under the acute treatment time period used in the labeling assays, (1) was not generally cytotoxic at concentrations up to 40 μM as determined by two independent cellular viability assays. Hence, decreases in serine labeling are a direct effect of (1) mediated PHGDH inhibition.

Compound (1) was used in a dose response experiment employing the same acute treatment method described herein. Serine labeling was significantly decreased at 30 μM and trended towards a decrease at 15 μM. Perturbations in labeling were specific to serine in that neither the PHGDH substrate, 3-PG, nor the end products of glycolysis, pyruvate and lactate, was affected. It was further confirmed that glycolytic metabolites were unperturbed by (1) treatment using LC-MS/MS to interrogate a greater panel of metabolites. Thus, changes in serine labeling are a direct effect of (1) mediated PHGDH inhibition and not a consequence of changes in PHGDH substrate levels or general perturbations in glycolytic flux. The absence of an effect on lactate labeling was consistent with the in vitro data showing that (1) does not inhibit LDH under the drug concentrations used. In sum, the data argue that (1) is able to selectively inhibit serine synthesis in cells.

Given that (1) is an ethyl ester and therefore susceptible to intracellular esterases, whether the carboxylic acid derivative of the parent molecule was still active against PHGDH was investigated; were the acid less active, it would likely decrease the efficiency of targeting PHGDH in situ. Parent and acid derivatives were equally potent against and selective for PHGDH in vitro suggesting that intra-cellular desertification is unlikely to affect (1) activity.

Compound (1) Selectively Inhibits the Proliferation of Cancer Cells with a High Propensity for Serine Synthesis.

A system to test the ability of (1) to inhibit PHGDH-dependent cancer cell proliferation was established that first evaluated the ability of a panel of breast and melanoma cell lines to proliferate in serine replete or deplete media as a proxy for serine biosynthetic activity. Breast lines were selected based on PHGDH expression according to the Cancer Cell Line Encyclopedia (CCLE) data and validated by blotting for PHGDH. Removing extracellular serine had no effect on proliferation of high PHGDH expressing lines: MDA-MB-468, MDA-MB-436, HCC70, and Hs578T. All four lines cluster in the top quartile of the CCLE data set for PHGDH expression; MDA-MB-468 and HCC70 cells harbor PHGDH amplifications. In contrast, serine depletion almost completely abrogated proliferation of low PHGDH expressing lines: MDA-MB-231 and MCF10A. In melanoma cells, PHGDH protein levels were similarly commensurate with the ability to proliferate in serine free media. Interestingly, although Carney cells are sensitive to extracellular serine depletion, they can adapt and proliferate as evidenced by increased PHGDH protein levels upon serine depletion.

Given that the ability to proliferate in the absence of extra-cellular serine is indicative of a high propensity for serine synthesis, it is possible that such lines should be sensitive to (1). Conversely, lines that cannot grow in serine free media have a low propensity for serine synthesis and should therefore be resistant to PHGDH inhibition. Treating the breast lines with (1) in serine replete media inhibited growth of the four lines that grew without extra-cellular serine in a dose dependent manner with growth inhibition ranging from 35% to 60% at 30 µM (1) as shown in FIG. 4, panel A. In FIG. 4, panel C, one can see that cell lines that rely on serine synthesis are most affected by the treatment with compound (1), in a dose-dependent manner. And lines that do not rely on the serine synthesis are minimally affected as shown in panel A The inhibitor had no effect on the three lines sensitive to serine withdrawal indicating that the inhibitor was selectively toxic to cells with high serine synthesis activity as shown in FIG. 4, panel A.

Whether removing serine from the media, to enhance the reliance on de novo serine synthesis, could sensitize cells to PHGDH inhibition was studied next. See FIG. 4, panel B. Indeed, serine depletion increased the efficacy of (1) in lines already sensitive under serine replete conditions as evidenced by an 80% to 90% decrease in proliferation with 30 µM (1). Moreover, MCF7 cells, which were of intermediate sensitivity to serine withdrawal, and insensitive to drug under serine replete conditions, became partially sensitive to the inhibitor under serine deplete conditions. Under serine replete conditions, PHGDH knockdown phenocopied the effects of (1) treatment in that the drug-sensitive lines were also sensitive to PHGDH knockdown as shown in FIG. 4, panel C. Furthermore, as with the drug treatments, growing cells in serine free media enhanced the growth inhibitory effect of PHGDH knockdown. See FIG. 4, panel D. Similar trends were observed for the melanoma panel in terms of both the selectivity of (1) for cells with a high propensity for serine synthesis and the increased efficacy under serine deplete conditions. Finally, the add derivative of compound (1) was not effective on MDA-MB-468 cells likely owing to poor membrane permeability.

Example 3: Study of Inhibition Modality

Analysis of (1) Inhibition Modality.

In an effort to more deeply characterize the mechanism by which (1) inhibits PHGDH, inhibition constants ($K_i$) for (1) with respect to each substrate were determined. (1) inhibited PHGDH in a non-competitive mode with respect to both substrates, as evidenced by a decreasing $V_{max}$ with increasing (1) concentration. The inhibition constants were 50±20 µM and 50±3 µM for 3PG and $NAD^+$, respectively. Also studied was whether there was any time dependence to the onset of inhibition by varying the time period for which drug and PHGDH were pre-incubated before initiating the enzymatic reaction. (1) was progressively more potent with increasing pre-incubation time culminating in an $IC_{50}$ of 7 µM when drug and PHGDH were pre-incubated for 4 hours. Intrigued by the combination of a time dependent onset of inhibition and non-competitive inhibition, the latter suggesting that (1) might be binding to an allosteric pocket, it was speculated that (1) could be affecting the PHGDH oligomerization state, where the time dependency of inhibition could potentially stem from drug-induced conformational changes in PHGDH. To evaluate the PHGDH oligomerization state, PHGDH was incubated with drug and then cross-linked prior to SDS-PAGE. (1) shifted the PHGDH equilibrium from the tetrameric to the dimeric state. No such effect was observed with LDH which is resistant to (1) mediated inhibition. (1) still inhibited a truncated form of PHGDH, which lacks the C-terminal domain responsible for tetramerization and is therefore a constitutive dimer. While not being bound by any particular theory, together these results suggest that disruption of the tetramer might assist PHGDH inhibition, but is not necessary for inhibition.

Example 4: PHGDH Knockdown Constructs

MDA-MB-468 (468) breast cancer cells (PHGDH amplified) were grown in DMEM supplemented with FBS (10%), penicillin, and streptomycin. 468 cells stably expressing PHGDH knockdown constructs were generated by infecting 468 cells with lentivirus harboring pLKO.1 shRNAs against PHGDH (sh29) or (sh31) and a nontargeting control (shGFP). Following infections, cells were selected for 2 days using puromycin prior to seeding in 10 cm plates for the experiment. PHGDH knockdown cells (sh29 and sh31) were seeded in 10 cm plates, each in triplicate, and shGFP cells in sextuplet. The following day, the media were changed and compounds (1) (30 µM) was added to 3 shGFP cell plates and an equivalent volume of DMSO to the other 9 plates to control for vehicle treatment. After 24 hours of treatment, the media were aspirated, and cells were washed with cold PBS prior to flash freezing. Subsequently, polar metabolites were extracted with 80% methanol for 30 minutes, scraped, transferred to Eppendorf tubes, centrifuged to remove insoluble matter, and dried. Samples were then re-suspended in 15 µL of HPLC grade water and analyzed by LC-MS/MS as described in Ying, H., et al., *Cell* 149: 656-670 (2012); and Yuan, M., et al., *Nature Protocols* 7: 872-881 (2012), each of which publications is incorporated by reference as if fully set forth herein. Briefly, samples were injected and analyzed using a 5500 QTRAP triple quadrupole mass spectrometer (AB/Sciex) coupled to a Prominence UFLC system (Shimadzu). Approximately 250 metabolites were analyzed by single reaction monitoring (SRM).

Metabolites significantly changed (fold change vs. control) relative to the nontargeting control (shGFP) for each of the 3 experimental conditions (sh29, sh31, compound (1)) were determined. A Venn-Diagram (FIG. 1) was generated depicting the results to indicate the number of changed metabolites that are changed uniquely or in common across the different conditions. There was significant overlap in the metabolites changed following drug treatment when compared to the different two shPHGDH treatments indicating that compound (1) mediated and genetic ablation of the pathway are similar phenotypically. Importantly, only 20 metabolites were uniquely changed in the compound (1) treatment, compared to 37 and 16 metabolites uniquely changed in sh29 and sh31, respectively. While not being bound by any specific theory, it is believed that these results demonstrate that the effects of the drug are primarily on target and that the off-target effects of the drug are commensurate with the off-target effects of using different shRNAs against the same target gene.

Figure 2:
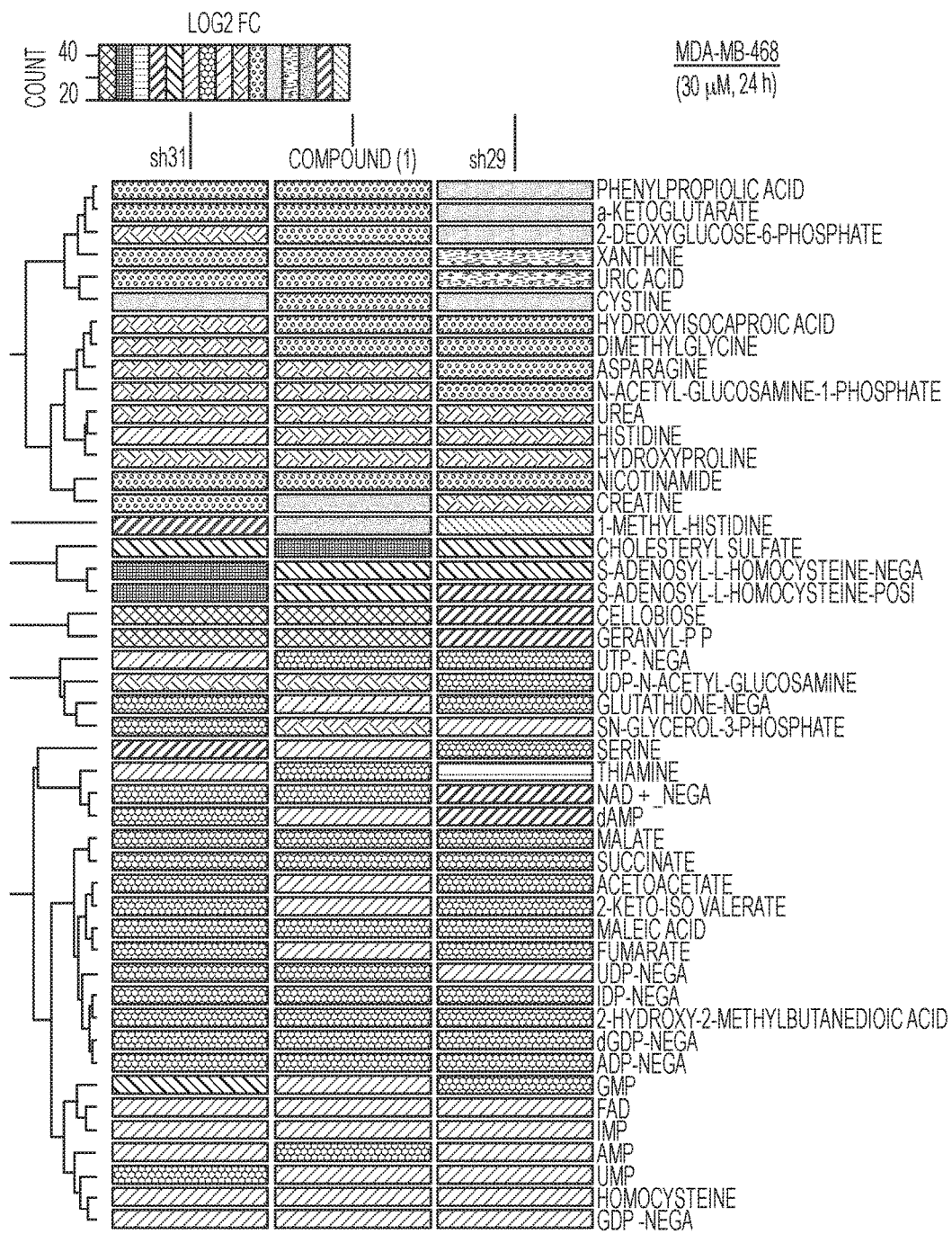
FIG. 2 is a "heat map" of metabolites commonly changed in shRNA treatments versus treatment with compound (1). Blue indicates a decrease relative to control (shGFP) hairpin, whereas red indicates an increase relative to control (shGFP) hairpin.

Focusing specifically on the metabolites that are changed in common across the 3 groups reveals that the direction of the changes (decrease/increase/no change) overlay extremely well when comparing drug to shRNA treatments. Indeed, of the 47 metabolites commonly changed only glutathione level changes differ in the drug treatment relative to the shRNA treatments. Importantly, serine, the direct product of the PHGDH pathway, is decreased in the drug treatment similarly to the shRNA treatments. While not being bound by any specific theory, these results suggest that the drug is engaging the target in cells. Furthermore, multiple purine metabolites, which are known to be downstream products of serine (via glycine and folate cycle one carbon units), are down regulated in both the drug and shRNA treatments, as shown in FIG. 2. For example: AMP, ADR, dAMP, IMP, GDP, dGDP, GMP levels are all decreased. In FIG. 2, red indicates that fold change increased relative to shGFP; blue indicates that fold change decreased relative to GFP; and the intensity of the color is proportional to the magnitude of the change.

Figure 3:
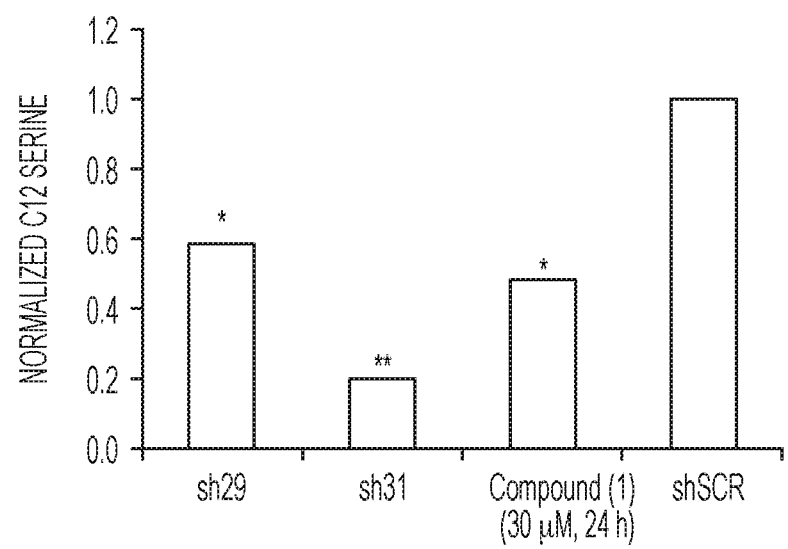
FIG. 3 is a histogram plotting the relative levels of intracellular serine normalized to the levels of serine in the control treatment.
Figure 4B:
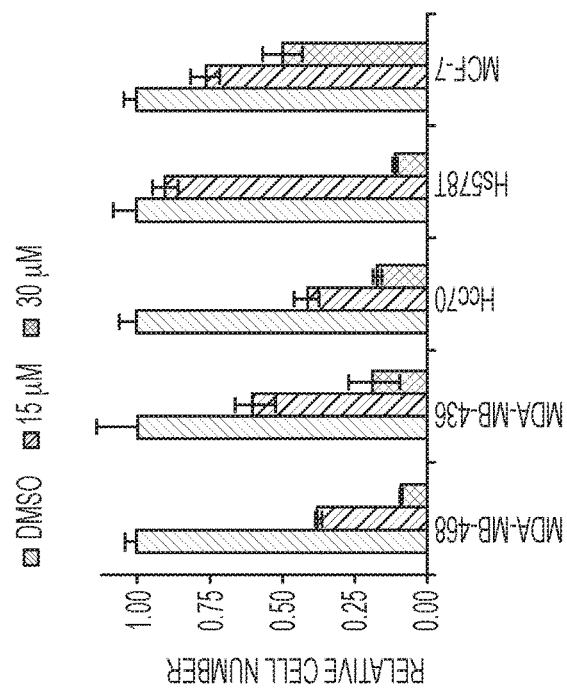
FIGS. 4A-D are histograms of relative cell numbers as a function of cell line and compound (e.g., compound (1), described herein) concentration. Panels A and C show proliferation assays for cell lines treated with compound (1) in serine replete media, whereas panels B and D show proliferation assays for cell lines treated with compound (1) in serine depleted media. Panels C and D show the results from experiments in serine replete media with PHGDH knockdown (sh1 and sh2) or a nontargeting control (shGFP). MDA-MB-468 and HCC70 are PHGDH amplified. MCF-10A cells are non-transformed mammary epithelial cells, other lines are cancer cell lines. MDA-MB-231 and MCF-10A lines were not included in serine depleted experiments in panels B and D because they are sensitive to serine withdrawal. Histograms depict mean±standard of error (n is greater than or equal to 3).
Figure 4A:
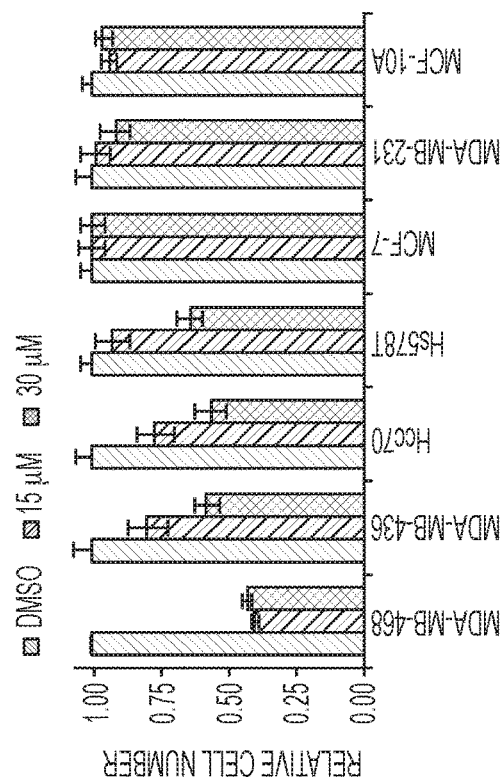
Figure 4D:
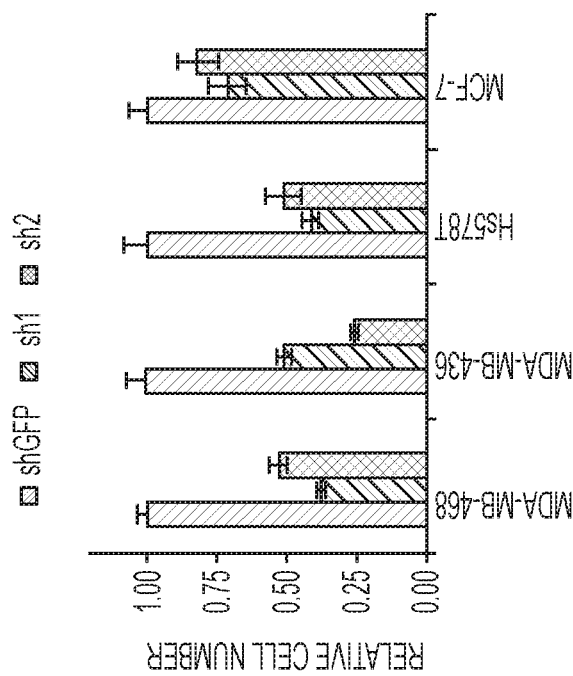
Figure 4C:
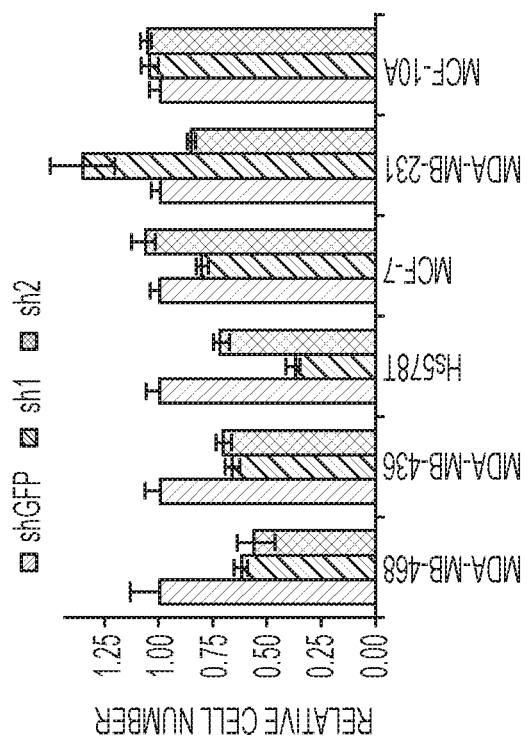

Specific comparison of changes in serine levels in drug versus knockdown treatments were undertaken. FIG. 3 is a histogram plotting the relative levels of intracellular serine normalized to the levels of serine in the control treatment. Importantly, compound (1) treatment is able to decrease intracellular serine levels by 50% commensurate with the effects of sh29. The bars depict the average fold change (n=3) and the significance value is indicated with asterisks, where * indicates p<0.05; and ** indicates p<0.01.

Example 5: Relative mRNA Expression Levels of PHGDH in Cancer Cell Lines

Figure 5:
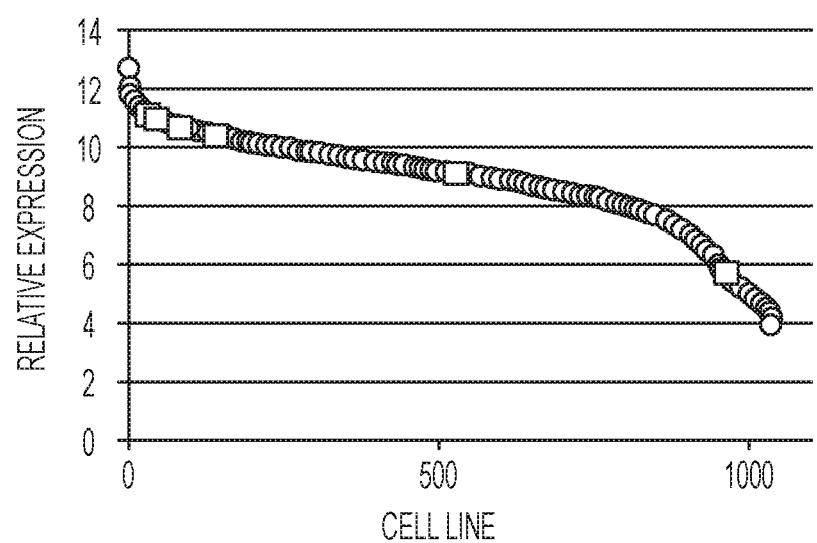
FIG. 5 is a plot of relative PHGDH expression as a function of cell line, across the Cancer Cell Line Encyclopedia (CCLE) data.

Relative mRNA expression levels of PHGDH across a panel of 1000 cancer cell lines profiled by the Cancer Cell Line Encyclopedia ("the Encyclopedia"; http://software.broadinstitute.org/software/cprg/?n-node/11, accessed 23 Dec. 2016) were evaluated and sorted from highest expressing to lowest expressing. Barretina et al., *Nature* 483: 603-7 (2012), which is incorporated by reference as if fully set forth herein. mRNA expression levels were determined using an Affymetrix Human Genome U133 Plus 2.0 Array as described in Barretina et al., *Nature* 483: 603-7 (2012). The cell lines described herein are included in the Encyclopedia and are cell lines that were experimentally tested for sensitivity to PHGDH knockdown/chemical inhibition herein and in Mullarky et al., *Proceedings of the National Academy of Sciences* 113: 1778-1783 (2016), which is incorporated by reference as if fully set forth herein. The cell lines included Hs578T (breast cancer); MDAMB468 (breast cancer); Hcc70 (breast cancer); MDAMB 436 (breast cancer); MCF7 (breast cancer); 143B (bone cancer); FU97 (stomach cancer); MORCPR (lung cancer); QGP1 (pancreatic cancer); and OV90 (ovarian cancer). The information is also presented in graphical form in FIG. 5, where each point is a cell line and the cell lines tested are shown as squares and the others as circles. In general, sensitivity to PHGDH inhibition correlates with PHGDH expression. DeNicola, et al., *Nature Genetics* 47: 1475-1481 (2015). Indeed the highest expressing cells, such as 468, Hcc70, Hs578T, 436, having an expression level from about 10 to 13 are sensitive to PHGDH inhibition; cell such as MCF7 cells, having an expression level of about 7 to about 9 are intermediary in their phenotype, in that they have an intermediate sensitivity to PHGDH inhibition; and cells such as 231 cells having an expression level of 6 or less are considered to be insensitive to PHGDH inhibition. Some embodiments are therefore directed to methods for inhibiting 3-phosphoglycerate dehydrogenase (PHGDH) in a cellular environment comprising cells having a PHGDH expression level of from about 7 to about 13 (e.g., from about 7 to about 12, about 8 to about 11, about 9 to about 13 or about 8.5 to about 11.5) comprising contacting the cellular environment with one or more of the compounds described herein (e.g., compounds of the general formula (I)).

The present invention provides for the following embodiments, the numbering of which is not to be construed as designating levels of importance:

Embodiment 1 relates to a compound of the formula (I):

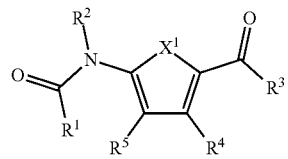

or a pharmaceutically acceptable salt, polymorph, prodrug, solvate or clathrate thereof, wherein: $R^1$ is substituted or unsubstituted aryl, substituted or unsubstituted arylalkyl or substituted or unsubstituted heteroaryl; $R^2$ is hydrogen or substituted or unsubstituted alkyl; $X^1$ is O or S; $R^3$ is —$NR^6R^7$ or —$OR^6$, wherein $R^6$ and $R^7$ are each, independently, hydrogen or substituted or unsubstituted alkyl; $R^4$ is substituted or unsubstituted aryl or substituted or unsubstituted alkyl; and $R^5$ is hydrogen, halo, —C≡N or —$SR^8$, wherein $R^8$ is hydrogen, substituted or unsubstituted alkyl, substituted or unsubstituted aryl or —C≡N. In other embodiments, $R^5$ is hydrogen, halo, —C≡N or —$SR^8$, wherein $R^8$ is hydrogen, substituted or unsubstituted alkyl, substituted or unsubstituted aryl or —C≡N.

Embodiment 2 relates to the compound as in Embodiment 1, wherein $X^1$ is S.

Embodiment 3 relates to the compound as in Embodiments 1-2, wherein $R^1$ is substituted or unsubstituted heteroaryl.

Embodiment 4 relates to the compound as in Embodiment 1-3, wherein the substituted or unsubstituted heteroaryl is furanyl.

Embodiment 5 relates to the compound as in Embodiments 1-2, wherein $R^1$ is substituted or unsubstituted aryl.

Embodiment 6 relates to the compound as in Embodiments 1-5 wherein $R^2$ is hydrogen.

Embodiment 7 relates to the compound as in Embodiments 1-6, wherein $R^3$ is —$OR^6$ and $R^4$ is substituted or unsubstituted alkyl.

Embodiment 8 relates to the compound as in Embodiment 7, wherein $R^6$ is substituted or unsubstituted alkyl.

Embodiment 9 relates to the compound as in Embodiments 1-8, wherein $R^5$ is —$SR^8$.

Embodiment 10 relates to the compound as in Embodiment 9, wherein $R^8$ is —C≡N.

Embodiment 11 relates to the compound as in Embodiment 1, which is selected from the group consisting of:

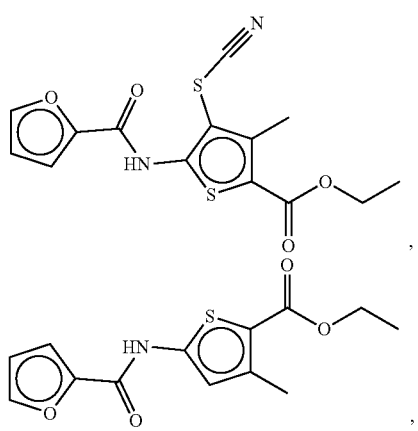

-continued

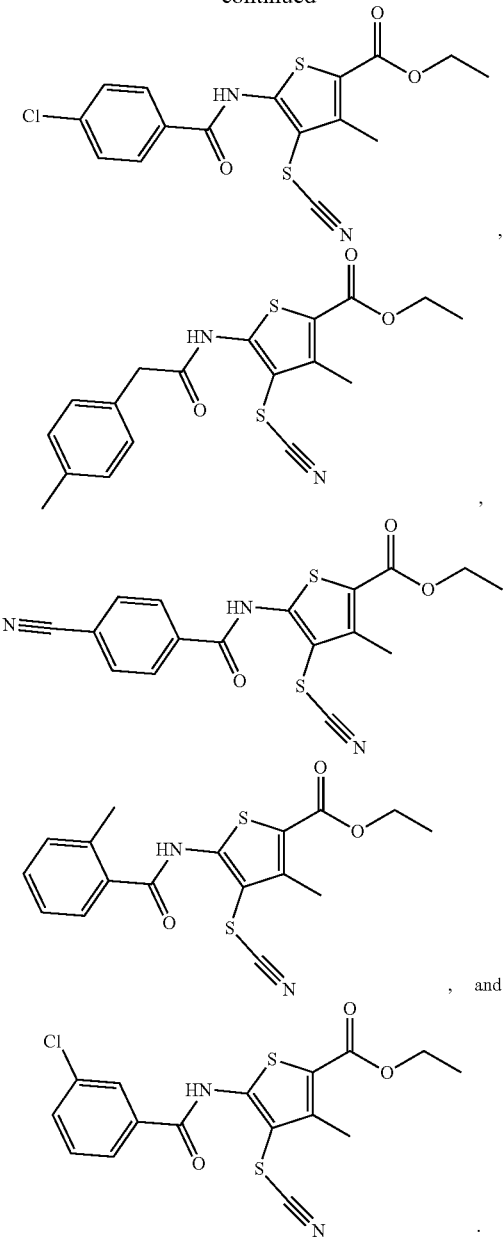

,

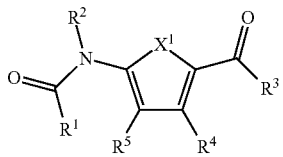

, and

.

Embodiment 12 relates to a pharmaceutical composition comprising a compound of Embodiments 1-11 and a pharmaceutically acceptable excipient.

Embodiment 13 relates to a method for treating cancer comprising administering a therapeutically effective amount of a compound of Embodiment 1; a pharmaceutical composition of Embodiment 12; or a pharmaceutical composition of Embodiment 12, wherein the pharmaceutical composition comprises a therapeutically effective amount of a compound of Embodiment 1.

Embodiment 14 relates to a method of inhibiting 3-phosphoglycerate dehydrogenase (PHGDH) in a cellular environment comprising contacting the cellular environment with an effective amount of a compound of Embodiment 1.

Embodiment 15 relates to a compound of the formula (I), as in Embodiments 1-11, for use as a medicament for treating a patient in need of relief from cancer.

Embodiment 16 relates to a compound of the formula (I), as in Embodiments 1-11, wherein the compound is at least 4-fold, at least 10-fold, or at least 100-fold more selective for PHGDH than other NAD(P)+ dependent dehydrogenases.

Embodiment 17 relates to the compound of Embodiment 16, wherein the other NAD(P)+ dependent dehydrogenases are selected from the group consisting of lactate dehydrogenase (LDH), 3α-hydroxysteroid dehydrogenase (3α-HSD), diaphorase, isocitrate dehydrogenase (IDH1), and malate dehydrogenase (MDH1).

Embodiment 18 relates to a method for inhibiting 3-phosphoglycerate dehydrogenase (PHGDH) in a cellular environment comprising cells having a PHGDH expression level of from about 7 to about 13 comprising contacting the cellular environment with one or more of the compounds of the formula (I), as in Embodiments 1-11.

What is claimed is:
1. A compound of the formula (I):

or a pharmaceutically acceptable salt thereof,
wherein:
$R^1$ is substituted or unsubstituted aryl, substituted or unsubstituted arylalkyl or substituted or unsubstituted heteroaryl;
$R^2$ is hydrogen or substituted or unsubstituted alkyl;
$X^1$ is O or S;
$R^3$ is —$NR^6R^7$ or —$OR^6$, wherein $R^6$ and $R^7$ are each, independently, hydrogen or substituted or unsubstituted alkyl;
$R^4$ is substituted or unsubstituted aryl or substituted or unsubstituted alkyl; and
$R^5$ is halo or —$SR^8$, wherein $R^8$ is hydrogen, substituted or unsubstituted alkyl, substituted or unsubstituted aryl or —C≡N.

2. The compound as in claim 1, or a pharmaceutically acceptable salt, wherein $X^1$ is S.

3. The compound as in claim 2, or a pharmaceutically acceptable salt, wherein $R^1$ is substituted or unsubstituted heteroaryl.

4. The compound as in claim 3, or a pharmaceutically acceptable salt, wherein the substituted or unsubstituted heteroaryl is furanyl.

5. The compound as in claim 2, or a pharmaceutically acceptable salt, wherein $R^1$ is substituted or unsubstituted aryl.

6. The compound as in claim 2, or a pharmaceutically acceptable salt, wherein $R^2$ is hydrogen.

7. The compound as in claim 6, or a pharmaceutically acceptable salt, wherein $R^3$ is —$OR^6$ and $R^4$ is substituted or unsubstituted alkyl.

8. The compound as in claim 7, or a pharmaceutically acceptable salt, wherein $R^6$ is substituted or unsubstituted alkyl.

9. The compound as in claim 7, or a pharmaceutically acceptable salt, wherein $R^5$ is —$SR^8$.

10. The compound as in claim 9, or a pharmaceutically acceptable salt, wherein $R^8$ is —C≡N.

11. The compound as in claim 1, or a pharmaceutically acceptable salt, which is selected from the group consisting of:
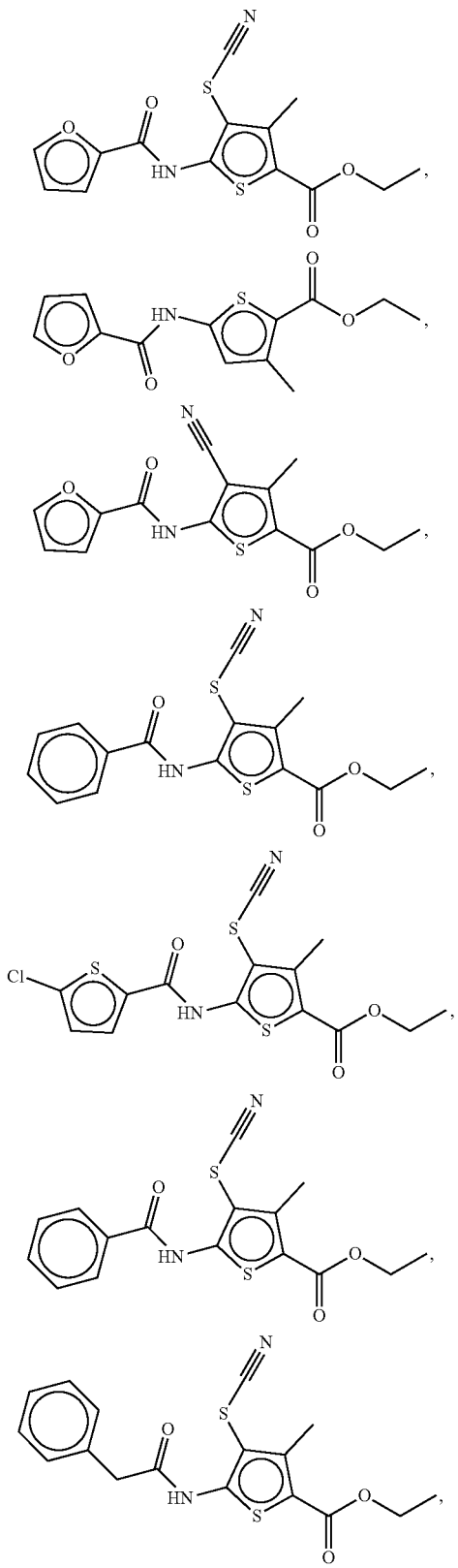
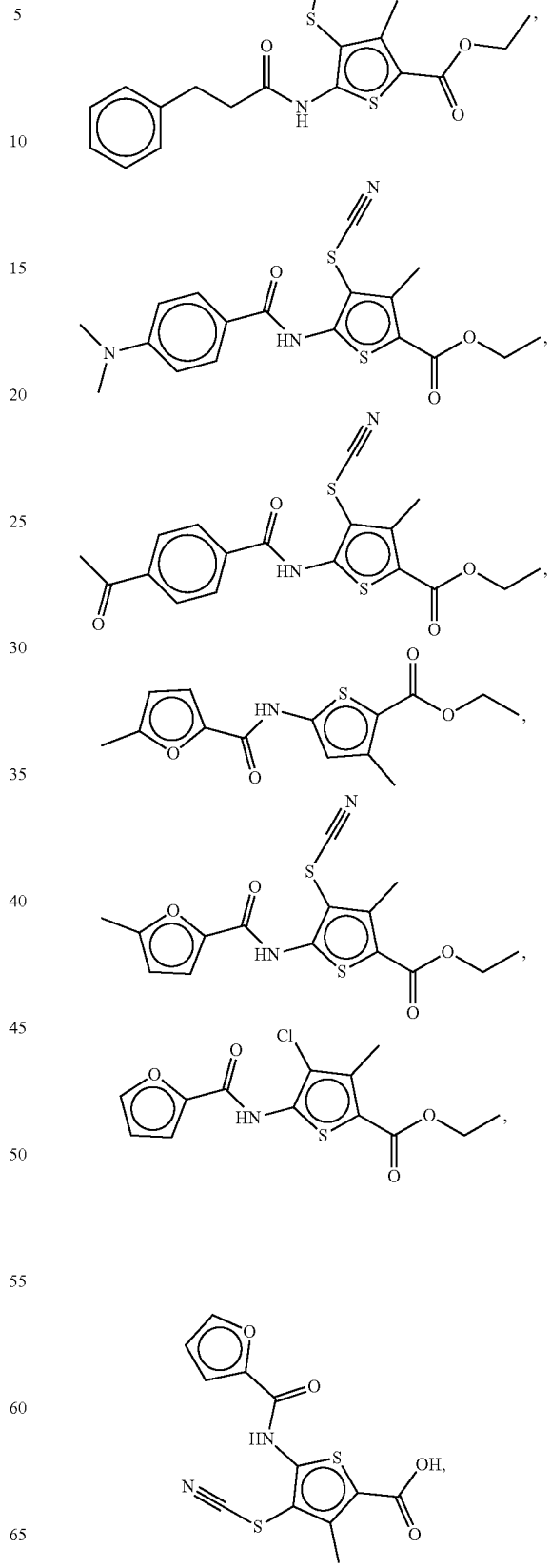

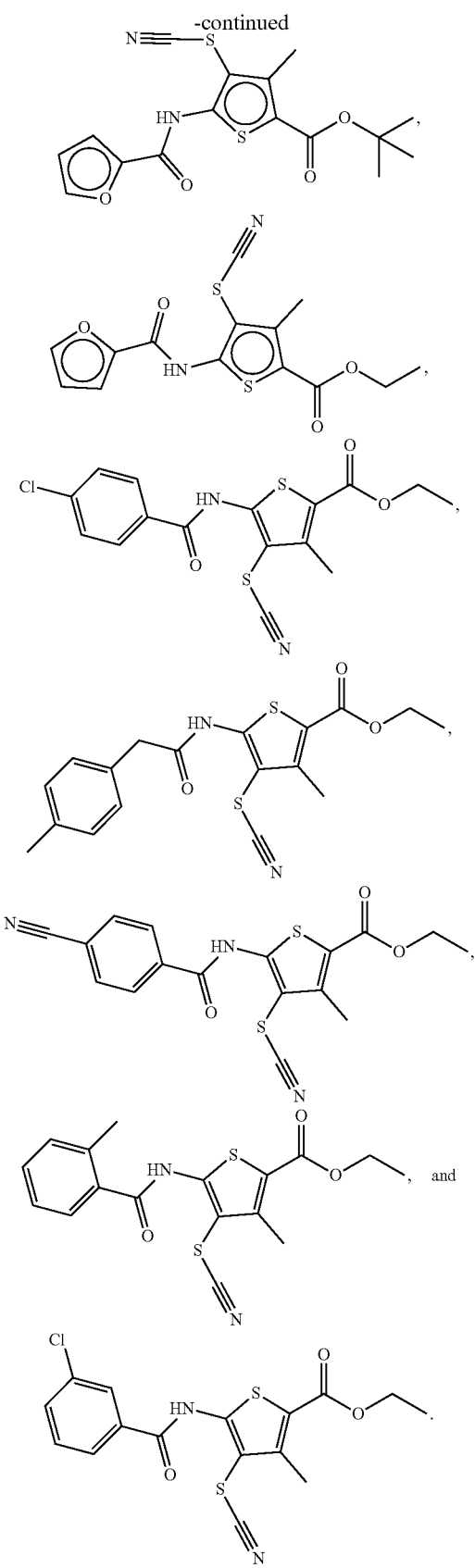

12. A pharmaceutical composition comprising a compound of claim 1, or a pharmaceutically acceptable salt thereof and a pharmaceutically acceptable excipient.

13. A method for treating breast, bone, ovarian, stomach, lung, and pancreatic cancer, comprising administering a therapeutically effective amount of a compound of claim 1, or a pharmaceutically acceptable salt thereof.

14. A method of inhibiting 3-phosphoglycerate dehydrogenase (PHGDH) in a cellular environment comprising contacting the cellular environment with an effective amount of a compound of the formula (I):

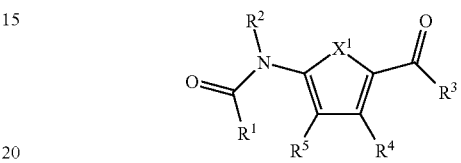

or a pharmaceutically acceptable salt thereof,
wherein:

$R^1$ is substituted or unsubstituted aryl, substituted or unsubstituted arylalkyl or substituted or unsubstituted heteroaryl;

$R^2$ is hydrogen or substituted or unsubstituted alkyl;

$X^1$ is O or S;

$R^3$ is —$NR^6R^7$ or —$OR^6$, wherein $R^6$ and $R^7$ are each, independently, hydrogen or substituted or unsubstituted alkyl;

$R^4$ is substituted or unsubstituted aryl or substituted or unsubstituted alkyl; and $R^5$ is hydrogen, halo, —C≡N or —$SR^8$, wherein $R^8$ is hydrogen, substituted or unsubstituted alkyl, substituted or unsubstituted aryl or —C≡N.

15. The method as in claim 14, wherein $X^1$ is S.

16. The method as in claim 15, wherein $R^1$ is substituted or unsubstituted heteroaryl or substituted or unsubstituted aryl.

17. The method as in claim 14, wherein $R^5$ is —$SR^8$.

18. The method as in claim 17, wherein $R^5$ is —C≡N.

19. A compound of the formula (I), as in claim 1, or a pharmaceutically acceptable salt thereof, wherein the compound is at least 4-fold, at least 10-fold, or at least 100-fold more selective for PHGDH than other NAD(P)⁺ dependent dehydrogenases.

20. The compound of claim 19, or a pharmaceutically acceptable salt thereof, wherein the other NAD(P)⁺ dependent dehydrogenases are selected from the group consisting of lactate dehydrogenase (LDH), 3α-hydroxysteroid dehydrogenase (3α-HSD), diaphorase, isocitrate dehydrogenase (IDH1), and malate dehydrogenase (MDH1).

21. A method for inhibiting 3-phosphoglycerate dehydrogenase (PHGDH) in a cellular environment comprising cells having a PHGDH expression level of from about 7 to about 13 comprising contacting the cellular environment with one or more of the compounds of the formula (I), as in claim 1, or a pharmaceutically acceptable salt thereof.

\* \* \* \* \*

UNITED STATES PATENT AND TRADEMARK OFFICE
CERTIFICATE OF CORRECTION

PATENT NO. : 10,494,365 B2
APPLICATION NO. : 16/067141
DATED : December 3, 2019
INVENTOR(S) : Cantley et al.

It is certified that error appears in the above-identified patent and that said Letters Patent is hereby corrected as shown below:

On the Title Page

In Column 2, item (56) under "Other Publications", Line 29, delete "Identfication" and insert --Identification-- therefor In the Claims In Column 32, Line 46, in Claim 18, delete "$R^5$" and insert --$R^8$-- therefor Signed and Sealed this
Fourth Day of August, 2020

Andrei Iancu
*Director of the United States Patent and Trademark Office*